United States Patent [19]

Guzek

[11] 4,073,907
[45] Feb. 14, 1978

[54] STABILIZED AMINOPHYLLINE SOLUTION AND PROCESS THEREFOR

[75] Inventor: David Thaddeus Guzek, Waukegan, Ill.

[73] Assignee: Abbott Laboratories, North Chicago, Ill.

[21] Appl. No.: 691,269

[22] Filed: June 1, 1976

[51] Int. Cl.$^2$ .............................................. A61K 31/52
[52] U.S. Cl. ................................................... 424/253
[58] Field of Search ......................................... 424/253

[56] References Cited
PUBLICATIONS

Drug & Cosmetic Industry, Feb. 1968, pp. 43–46 and 147–149.

*Primary Examiner*—Stanley J. Friedman
*Attorney, Agent, or Firm*—Robert L. Niblack; Neil E. Hamilton

[57] ABSTRACT

A stable aqueous aminophylline solution is provided by admixing with said solution disodium edetate as a chelating agent and removing substantially all the carbon dioxide from the solution. In a preferred manner the chelating agent is present in an amount of 0.01 to 1.0% by weight of the solution. Carbon dioxide is preferably removed to optimize aminophylline stability by boiling the solution under an inert gas protection. A stabilized aqueous aminophylline solution results which can be packaged in a container system which would otherwise have a propensity to develop undesired crystal growth in the solution.

7 Claims, No Drawings

STABILIZED AMINOPHYLLINE SOLUTION AND PROCESS THEREFOR

BACKGROUND OF THE INVENTION

This invention relates to stabilized aqueous aminophylline solutions. More particularly, it relates to a process and stabilized aminophylline solution wherein disodium edetate is added to the solution as a chelating agent in a preferred amount of 0.01 to 1.0% by weight and carbon dioxide is removed from the aqueous aminophylline solution so as to substantially prevent crystal growth in the aminophylline solution when it is packaged in a ready-to-use container system.

Aqueous aminophylline solutions are useful in I.V. administration as diuretics, cardiotonics and as respiratory stimulants. In the past, this product has not been prone to exhibit instability when packaged in a single-dose ampoule. Recently, however, demands for ready-to-use packaging and emergency drug solutions such as ready-to-use vials and syringes tend to promote undesired crystal growth. This crystal growth is totally unacceptable from the standpoint of efficacy, pharmaceutical elegance, possible loss of potency and the safety required of all parenterals. The crystal information has been found to be a function of an interaction between the drug and stopper. The growth of the crystals is not a function of stopper incompatability, but instead a chemical phenomenon due to the ability of the disassociated drug to complex with divalent ions available in the stopper. This is supported by the observation that the crystals developed in the packaging system in question first occur at the solution - stopper interface.

The U.S. Pharmacopeia advises as to the avoidance of carbon dioxide in containers for aminophylline. An article entitled "Antioxidants and Chelating Agents as Stabilizers in Liquid Dosage Forms" by Leon Lachman in *Drug and Cosmetic Industries*, Vol. 102, page 43 (February, 1968), as the title implies, utilizes antioxidants and chelating agents to enhance the stability of pharmaceutical liquids. However, it should be pointed out that quite unexpectedly it was found that a compound closely chemically related to the chelating of this invention, calcium disodium edetate, will not prevent crystal development in a container system for aqueous aminophylline, where metal ions are present.

It is an advantage of the present invention to provide a stabilized aminophylline aqueous solution and a method for providing such solution. Other advantages are a stabilized aqueous aminophylline solution which can be packaged in ready-to-use stoppered vials wherein crystal growth of the solution as effected by the stopper is eliminated, an aqueous aminophylline solution which when packaged in a stoppered container will maintain efficacy, pharmaceutical elegance, high potency and safety for the parenteral solution.

SUMMARY OF THE INVENTION

The foregoing advantages are accomplished and the shortcomings of the prior art are overcome by the present process and product produced therefrom, wherein an aqueous aminophylline solution tending to promote crystal growth when in contact in a container system has added thereto disodium edetate as a chelating agent and carbon dioxide is removed from the solution. The resulting solution is maintained substantially free of carbon dioxide and the carbon dioxide is removed by boiling the aminophylline solution under the protection of an inert gas atmosphere with filling of the container being effected under an inert gas protection. The disodium edetate chelating agent is preferably added in an amount of 0.01 to 1.0% by weight based on the final solution.

The following examples are set forth for the purpose of illustrating the present invention and should not be construed to limit the invention to the precise ingredients, proportions, temperatures or other conditions specified.

EXAMPLE I

A typical formula for a stabilized injectable aminophylline solution having a concentration of 25 mg./ml. is:

| Ingredient | Amount Per Liter |
| --- | --- |
| Aminophylline U.S.P.* (Powder) | 25.00 g. |
| Ethylenediamine U.S.P. | Sufficient for pH adjustment |
| Disodium Edetate U.S.P.* | 1.0 g. |
| Nitrogen Gas U.S.P. | q.s. |
| Water for Injection | q.s. 1000 ml. |

*Factored to anhydrous basis.

The solution is prepared in a glass-lined or stainless steel tank. The water is heated to boiling in the tank by suitable means to dispel carbon dioxide. The headspace in the tank is gassed with nitrogen gas and the water cooled to 80° C. Approximately 20% of the final volume of the previously heated water is transferred to a suitable glass-lined or stainless steel tank and held under nitrogen protection while maintaining the temperature of the water in the range of 75° - 85° C.

The aminophylline powder is added to the 80% portion of the water while mixing and avoiding vortex during mixing with nitrogen protection being provided at all times. The disodium edetate is added to the resulting solution with mixing and the pH of the solution observed. Ethylenediamine is added to the previously formed solution with mixing to result in a pH in the range of 8.6 to 9.0. Sufficient previously boiled, nitrogen protected water for injection is added to desired final volume and the solution mixed until a uniform solution is accomplished. The pH of the solution is again observed and adjusted to a range of 8.6 to 9.0 with the ethylenediamine. The previously prepared solution is filtered using an approved membrane and held warm, while being protected with headspace nitrogen protection.

The aminophylline solution is suitably filled in stoppered glass vials of the type described in U.S. Pat. No. 3,376,866 which illustrates a glass vial closed with a resilient plug. The aminophylline solution should be protected with filtered nitrogen gas in the container headspace during the filling operation. Preferably the solution will be hot filled at a temperature range of 50° - 60° C. during prefilling storage and filling.

The following Examples II and III illustrate different concentrations of stabilized aminophylline solutions wherein the concentration of aminophylline and disodium edetate are varied. Example IV illustrates a typical production size batch. The same procedures are employed as indicated in Example I for combining the ingredients. As is stated in Example I the aminophylline, ethylenediamine and disodium edetate will be factored on an anhydrous basis and the water for injection should be freshly boiled and nitrogen protected.

EXAMPLE II

| Ingredient | Amount Per Liter |
| --- | --- |
| Aminophylline U.S.P. (Powder) | 4.00 g. |
| Ethylenediamine U.S.P. | Sufficient for pH adjustment |
| Disodium Edetate U.S.P. | 0.1 g. |
| Nitrogen Gas U.S.P. | q.s. |
| Water for Injection | q.s. 1000 ml. |

EXAMPLE III

| Ingredient | Amount Per Liter |
| --- | --- |
| Aminophylline U.S.P. (Powder) | 25.00 g. |
| Ethylenediamine U.S.P. | Sufficient for pH adjustment |
| Disodium Edetate U.S.P. | 10.0 g. |
| Nitrogen gas U.S.P. | q.s. |
| Water for Injection | q.s. 1000 ml. |

EXAMPLE IV

| Ingredient | Amount Per Liter |
| --- | --- |
| Aminophylline U.S.P. | 4.5 kg. |
| Ethylenediamine U.S.P. | Sufficient for pH adjustment |
| Disodium Edetate U.S.P. | 0.18 kg. |
| Water for Injection q.s. | 180 l. |

The effectiveness of the chelating agent when employed under the foregoing conditions of the Examples is indicated by the following test:

A solution is prepared containing theophylline and ethylenediamine at the concentration present in Aminophylline Solution U.S.P. (84 − 86% anhydrous theophylline and 14 − 15% ethylenediamine). The solution is divided in half and the disodium edetate added and dissolved in one solution. The two solutions are divided into three portions each and calcium chloride at 1 mg., 3 mg., and 5 mg. $Ca^{++}$/ml. was added. The solutions were sealed and stored at 50° C. for 24 hours and observed visually. All solutions without the disodium edetate exhibited crystal development. These solutions protected with disodium edetate were free of crystal development. Crystals formed during this accelerated study and those formed over long periods of room temperature storage were compared by I.R. analysis and found to be identical.

As indicated in the foregoing examples, the preferred amount of disodium edetate chelating agent is in the range of 0.01 to 1.0% by weight based on the total solution weight. While a temperature of 80° C. is indicated as preferred for heating the water during mixing of the aminophylline in solution, the temperature can be reduced to 60° C. without adverse effects. Nitrogen gas protection has been utilized as an inert gas media both during the boiling of the aminophylline solution as well as when adjusting the solution to final volume and packaging. Other inert gases such as helium or argon could also be employed.

It will thus be seen that through the present invention there is provided a specific chelating agent for aqueous aminophylline solutions which can be packaged in a ready-to-use vial without undesired crystal growth. The method of obtaining the stabilized aminophylline solution can be effected without large investment for equipment, precise control of processing conditions and with readily available stabilizing materials.

The foregoing invention can now be practiced by those skilled in the art. Such skilled persons will know that the invention is not necessarily restricted to the particular embodiments presented therein. The scope of the invention is to be defined by the terms of the following claims as given meaning by the preceding description.

I claim:

1. A method of stabilizing and preventing undesired crystal growth in an aqueous aminophylline solution for contact with a container system tending to promote crystal growth comprising: forming a solution of aminophylline, water, and disodium edetate, said disodium edetate present in the amount of about 0.01 to about 1.0% by weight based on the total solution weight, admixing ethylenediamine to effect a pH in the resulting solution of about 8.6 to about 9.0, said water prior to mixing with said aminophylline and disodium edetate being substantially free of carbon dioxide and excluding substantially all carbon dioxide from said solution by means of inert gas protection, said disodium edetate chelating any metal ion being present in said solution to form a soluble material.

2. The method of claim 1 wherein said water is rendered free of carbon dioxide by boiling.

3. The method of claim 2 wherein said boiling is effected under an inert gas protection.

4. The method of claim 3 further including the filling of said container under inert gas protection.

5. The method as defined in claim 4 wherein said inert gas is nitrogen.

6. A stabilized aqueous aminophylline solution for contact with a container system tending to promote undesired crystal growth comprising: an aqueous aminophylline solution containing about 0.01 to about 1.0% by weight, based on the total solution weight, of disodium edetate as a chelating agent, said stabilized solution having removed therefrom substantially all carbon dioxide and including ethylenediamine to effect a pH of at least about 8.6 to about 9.0.

7. A stabilized aminophylline solution as defined in claim 6 wherein said solution further contains an inert gas.

* * * * *